United States Patent
Weisheit et al.

(10) Patent No.: US 6,720,163 B1
(45) Date of Patent: Apr. 13, 2004

(54) METHOD FOR DETERMINING ALKALINE PHOSPHATASE AND ELIMINATING HAEMOGLOBIN DISTURBANCES

(75) Inventors: Ralph Weisheit, Peissenberg (DE); Wolfgang Treiber, Weilheim (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/807,079

(22) PCT Filed: Oct. 5, 1999

(86) PCT No.: PCT/EP99/07394

§ 371 (c)(1),
(2), (4) Date: Apr. 6, 2001

(87) PCT Pub. No.: WO00/22162

PCT Pub. Date: Apr. 20, 2000

(30) Foreign Application Priority Data

Oct. 8, 1998 (DE) .................................. 198 46 301

(51) Int. Cl.⁷ ............................................. C12Q 1/42
(52) U.S. Cl. ................................... 435/21; 436/15
(58) Field of Search ....................... 435/4, 21, 967; 436/15, 164

(56) References Cited

U.S. PATENT DOCUMENTS

| 5,766,872 A | | 6/1998 | Cybulski | 435/22 |
| 6,013,467 A | * | 1/2000 | Siedel et al. | 435/25 |
| 6,207,459 B1 | * | 3/2001 | Weisheit et al. | 436/66 |

FOREIGN PATENT DOCUMENTS

| DE | 19622090 A1 | 12/1997 | G01N/33/50 |
| DE | 19628484 A1 | 1/1998 | G01N/33/72 |
| EP | 0695805 A2 | 2/1996 | C12Q/1/32 |
| WO | WO97/45728 | 12/1997 | G01N/33/487 |
| WO | WO 97/45732 | * 12/1997 | G01N/33/52 |
| WO | WO 97/45733 | * 12/1997 | G01N/33/52 |
| WO | WO97/45733 | 12/1997 | G01N/33/52 |
| WO | WO 98/02570 | * 1/1998 | C12Q/1/26 |

OTHER PUBLICATIONS

Jay, D.W. and Provasek, D., "Characterization and Mathematical Correction of Hemolysis Interference in Selected Hitachi 717 Assays", Clinical Chemistry, 39(9), 1804–1810, 1993.*

Chance, J.J., Norris, E.J. and Kroll, M.H., "Mechanism of Interference of a Polymerized Hemoglobin Blood Substitute in an Alkaline Phosphatase Method", Clinical Chemistry, 46(9), 1331–1337, 2000.*

B. Hahn, et al., "Polychromatic Analysis: New Applications of an Old Technique", Clin. Chem. 25/6, 951–959 (1979).

Dennis W. Jay, et al., "Characterization and Mathematical Correction of Hemolysis Interference in Selected Hitachi 717 Assays" Clin. Chem. 39/9, 1804–1810 (1993).

* cited by examiner

*Primary Examiner*—Ralph Gitomer
(74) *Attorney, Agent, or Firm*—Brinks Hofer Gilson & Lione

(57) ABSTRACT

The invention concerns a method for the determination of alkaline phosphatase in a sample by optical measurement in which interference by free haemoglobin or blood substitutes is eliminated by means of certain wavelength combinations, a method for eliminating interference caused by free haemoglobin or blood substitutes in a determination of alkaline phosphatase and the use of certain wavelength combinations to eliminate interference by free haemoglobin or blood substitutes.

21 Claims, No Drawings

METHOD FOR DETERMINING ALKALINE PHOSPHATASE AND ELIMINATING HAEMOGLOBIN DISTURBANCES

This application is filed as a 371 application and claims priority to PCT/EP99/07394 filed Oct. 5, 1999, which claims priority to Germany 198 46 301.4 filed Oct. 8, 1998.

BACKGROUND

The invention concerns a method for the determination of alkaline phosphatase in a sample by optical measurement in which interference by free haemoglobin or blood substitutes is eliminated by means of certain wavelength combinations, a method for eliminating interference caused by free haemoglobin or blood substitutes in a determination of alkaline phosphatase and the use of certain wavelength combinations to eliminate interference by free haemoglobin or blood substitutes.

It is known that haemolysis considerably interferes with some diagnostic methods for the determination of analytes. Haemolysis is understood as any destruction of erythrocytes for example by mechanical, osmotic, chemical or enzymatic action on the cell membrane of the erythrocytes. As a result of haemolysis, the blood pigment haemoglobin (Hb) is released and can no longer be removed from a sample. The presence of haemoglobin is problematic because, on the one hand, the absorption spectrum of haemoglobin in some cases overlaps considerably with the spectra of the substances to be detected and indicators (chromogens) which can result in measuring errors in photometric tests. On the other hand, haemoglobin can also react chemically with sample components to form substances which can also result in false measurements.

Recently blood substitutes whose manufacture is based on haemoglobin are being used more and more frequently for therapeutic purposes for example after a large loss of blood. The haemoglobin in blood substitutes can be native or synthetic. Often Hb-like compounds are also used. In contrast to haemolysis, the Hb content in blood, serum or plasma may be more than 2000 mg/dl during treatment with blood substitutes. Hence interference in samples which contain blood substitutes is often considerably more pronounced than in haemolytic samples since the haemoglobin or the synthetic analogue is in a free form right from the beginning.

Interference by free haemoglobin is particularly serious in the photometric determination of alkaline phosphatase. The formation of 4-nitrophenol is measured at 415 nm (increase of absorbance) for the determination of alkaline phosphatase. Haemoglobin also absorbs at 415 nm. The presence of haemoglobin interferes with the determination of alkaline phosphatase in two respects: On the one hand the Hb spectrum changes in a time-dependent manner (increase of absorbance) in an alkaline medium, on the other hand, the photometer limit of the measuring instrument is reached above a certain Hb content.

Various methods have been published in the prior art to eliminate the spectral and chemical influence of haemoglobin on the analysis of serum or plasma samples.

Due to the simple handling on automated analyzers, a second measuring wavelength (secondary wavelength) is often used in addition to the first measuring wavelength (main wavelength) in order to eliminate the interfering effect of interfering substances such as haemoglobin, bilirubin and lipaemia or to at least minimise this effect. In Clin. Chem. 25/6, 951–959 (1979) Hahn et al mention that the secondary wavelength should be selected such that it is near to the absorption minimum of the chromogen and near to the absorption maximum of the interfering substance. However, it is not possible to use the stated measuring procedures to eliminate interference in the determination of alkaline phosphatase.

Jay and Provasek (supra) describe a further method for eliminating interference by the so-called rate-blank measurement. The correction of haemolysis interference by rate-blank measurements is also described in EP-A-0 695 805, which is hereby incorporated by reference in its entirety. In this method the sample is subjected to a pre-reaction to determine the degree of haemolysis of the sample before the actual photometric determination of a component contained in the sample. The measured value obtained subsequently is then corrected by a value which has been determined by correlating the degree of haemolysis with the amount by which the interfering components contribute to the measuring error.

Although the mathematical correction mentioned by Jay and Provasek eliminates the influence of Hb up to at least 800 mg/dl Hb, it is, however, not very user-friendly since it requires an additional measurement of the Hb content and subsequently an additional mathematical correction step.

Jay and Provasek (supra) describe a further method for eliminating interference by the so-called rate-blank measurement. The correction of haemolysis interference by rate-blank measurements is also described in EP-A-0 695 805. In this method the sample is subjected to a pre-reaction to determine the degree of haemolysis of the sample before the actual photometric determination of a component contained in the sample. The measured value obtained subsequently is then corrected by a value which has been determined by correlating the degree of haemolysis with the amount by which the interfering components contribute to the measuring error.

Hb interference can be eliminated by rate-blank measurements but only up to a Hb content of ca. 1200 mg/dl since the photometer limit is reached at higher Hb contents. This may be adequate for eliminating haemolysis interference but it is not sufficient at all for eliminating interference by blood substitutes.

Another method for eliminating haemoglobin interference was published for the determination of albumin (PCT application WO 97/45728) in which an elimination of haemoglobin interference was achieved by special combinations of main and secondary wavelengths. However, the wavelength combinations mentioned in this PCT application cannot be used for the determination of alkaline phosphatase since a measuring signal would no longer be obtained for 4-nitrophenol at these wavelengths.

The laid-open publication WO 97/45733 describes that interference by haemoglobin can be eliminated by using the wavelengths 546 and 570 in individual UV tests. However, this method can only be used for enzymatic UV tests with a main measurement wavelength of 340 nm. Although a complete elimination of Hb interference can be achieved solely by the use of the secondary wavelengths 546 or 570 nm, this is not possible for enzymatic chromogenic tests such as the determination of alkaline phosphatase in which the main measurement wavelength is in the range of 415 nm.

The U.S. Pat. No. 5,766,872 mentions that a secondary wavelength of 577 nm reduces haemolysis interference in the amylase determination. However, the quoted measurement data show that there is already a significant deviation of the measured values of up to 8% at a Hb content of 500 mg/dl. This may be sufficient to eliminate haemolysis interference but it is probable that at higher Hb concentrations (such as those which occur during treatment with blood substitutes) this deviation of the measured values would become larger due to the use of a main measurement wavelength of ca. 415 nm and that there would no longer be an adequate elimination of Hb interference.

No method for the determination of alkaline phosphatase is known in the prior art which can also be carried out without interference in the presence of high concentrations of Hb such as those which occur in samples containing blood substitutes.

The object was therefore to develop an improved method for the determination of alkaline phosphatase in a sample which largely overcomes the disadvantages of the prior art. In particular it is intended to provide a simple and user-friendly method for eliminating interference by haemoglobin and by blood substitutes based on haemoglobin when determining alkaline phosphatase.

SUMMARY OF THE INVENTION

The object is achieved by a method described in more detail in the claims for the determination of alkaline phosphatase in a sample by optical measurement. The method is characterized in that 450±10 nm is used as a main measurement wavelength and at least one of the wavelengths 480±10 nm, 546±10 nm or 575±10 nm is used as the secondary measurement wavelength. Preferably only one of the said secondary measurement wavelengths is used.

It surprisingly turned out that Hb interference of the determination of alkaline phosphatase can be effectively eliminated when the main wavelength and also the secondary wavelength is changed. It is not sufficient for a satisfactory elimination of Hb interference to only change the main wavelength or only the secondary wavelength.

Due to the absorption spectrum of 4-nitrophenol it is possible to measure alkaline phosphatase not only at 415 nm but also at 450±10 nm. Although the main measurement wavelength is then not in the usual absorption maximum of the detection reaction but on its flank, the measured signal obtained is nevertheless adequate for an exact determination of alkaline phosphatase.

The selection of the new main measurement wavelength of 450±10 nm already leads to a slight reduction of the haemoglobin interference, but a complete elimination of interference is surprisingly only obtained by combining the main wavelength 450±10 nm with at least one of the secondary wavelengths 480±10 nm, 546±10 nm or 575±10 nm. A secondary wavelength of 570 nm has proven to be particularly suitable. The secondary wavelength of 480±10 nm has proven to be very suitable for eliminating Hb interference especially for the determination of alkaline phosphatase according to the IFCC method (example 2).

Other secondary wavelengths such as 340, 376, 505, 600, 660 and 700 nm have proven to be unsuitable for eliminating haemoglobin interference.

DETAILED DESCRIPTION OF THE INVENTION

The method according to the invention enables interference of the alkaline phosphatase determination by haemoglobin or haemoglobin-like compounds to be eliminated for the first time in a simple manner up to a Hb content of at least 3000 mg/dl. The upper limit for the elimination of Hb interference is the limit determined by the performance of the photometer. Hence the method according to the invention can be expected to achieve a good elimination of interference up to 6500 mg/dl haemoglobin content. Furthermore the invention can be applied to the various reagents for the determination of alkaline phosphatase as shown in examples 1 to 3.

The method according to the invention is suitable for a determination of any samples in which free haemoglobin is present. The term free haemoglobin in the sense of the invention is used to distinguish it from haemoglobin which is present in intact erythrocytes. Examples of samples that contain free haemoglobin are haemolytic serum or plasma samples or samples which contain blood substitutes. Examples of blood substitutes that fall under the term free haemoglobin in the sense of the present invention are derivatized, polymerized, modified or cross-linked derivatives of haemoglobin and in particular human haemoglobin or bovine haemoglobin e.g. DCL haemoglobin (diaspirin-crosslinked haemoglobin) or recombinantly produced haemoglobin.

The invention also concerns a method for eliminating interference caused by free haemoglobin in a method for determining alkaline phosphatase. The method is characterized in that 450±10 nm is used as a main measurement wavelength and at least one of the wavelengths 480±10 nm, 546±10 nm or 575±10 nm is used as a secondary measurement wavelength.

A further subject matter of the invention is the use of a main measurement wavelength of 450±10 nm in combination with at least one of the secondary measurement wavelengths 480±10 nm, 546±10 nm or 575±10 nm to eliminate interference by free haemoglobin or by blood substitutes manufactured on the basis of haemoglobin in a method for determining alkaline phosphatase.

The invention is elucidated by the following examples:

EXAMPLES

General Methods

A solution containing Hb was added to a part of a serum pool to yield a Hb content of at least 3000 mg/dl. Another part of the same serum pool of the same volume was admixed with an equivalent amount of NaCl solution (154 mmol/l). Both parts were subsequently mixed with one another in different ratios to obtain a Hb concentration series of 11 samples with no Hb in the lower sample and at least 3000 mg/dl Hb in the highest sample.

Example 1

Determination of Alkaline Phosphatase According to the SFBC Method

Determination according to the recommendation to the Société Francaise de Biologie Clinique according to Ann. Biol. Clin. Vol. 35, 271 (1977).

The determination was carried out on a Boehringer Mannheim/Hitachi 911 analyzer.

The following reagents were used:
reagent 1: 930 mmol/l 2-amino-2-methyl-1-propanol buffer pH 10.5;
1.03 mmol/l magnesium aspartate
reagent 2: 930 mmol/l 2-amino-2-methyl-1-propanol buffer, pH 10.5;
1.03 mmol/l magnesium aspartate;
98 mmol/l 4-nitrophenyl phosphate The test procedure was as follows: 250 µl reagent 1 was added to 11 µl sample and after 5 min 50 µl reagent 2 was added. The analyte was determined after a further 50 sec over a period of 4 min during which the change in absorbance was measured during this 4 min. Combinations of the following main measurement wavelengths ($\lambda_1$) and secondary measurement wavelengths ($\lambda_2$) were used for the measurement: $\lambda_1/\lambda_2$=415/546 nm, 415/570 nm, 415/660 nm and 450/660 nm, (comparison) and 450/546 nm and 450/570 nm (invention).

Alkaline phosphatase was determined by the rate blank measurement mentioned by Jay and Provasek as a further comparison (referred to as 415/660 nm RB).

The result is shown in table 1. It can be seen that when using the inventive measurement wavelength combinations of 450/546 nm or 450/570 nm the effect of haemoglobin is significantly reduced compared to the other measurement wavelength combinations or compared to the rate blank measurement.

The result is shown in table 2. It can be seen that when using the inventive measurement wavelength combination of 450/480 nm the effect of haemoglobin is significantly reduced compared to the previous measurement wavelength combination 415/700 nm and no negative values occur even at very high Hb contents.

TABLE 2

Measured content of alkaline phosphatase at 37° C. in U/l

| Hb content* [mg/dl] | 415/700 nm | 450/480 nm |
| --- | --- | --- |
| 0 | 167 | 170 |
| 300 | 157 | 164 |
| 600 | 152 | 160 |
| 900 | 145 | 157 |

TABLE 1

Measured content of alkaline phosphatase at 37° C. in U/l

| Hb content* [mg/dl] | 415/546 nm | 415/570 nm | 415/660 nm | 415/660 nm RB | 450/660 nm | 450/546 nm | 450/570 nm |
| --- | --- | --- | --- | --- | --- | --- | --- |
| 0 | 42 | 42 | 42 | 42 | 42 | 41 | 42 |
| 300 | 33 | 32 | 32 | 44 | 35 | 40 | 41 |
| 600 | 24 | 24 | 22 | 46 | 29 | 40 | 40 |
| 900 | 16 | 16 | 14 | 46 | 24 | 39 | 41 |
| 1200 | 11 | 11 | 8 | 44 | 22 | 40 | 40 |
| 1500 | 7 | 7 | 3 | 5 | 19 | 40 | 40 |
| 1800 | 2 | 2 | −2 | 0 | 17 | 39 | 40 |
| 2100 | 3 | 3 | −2 | 0 | 17 | 40 | 41 |
| 2400 | 3 | 3 | −2 | 1 | 15 | 43 | 42 |
| 2700 | 4 | 3 | −1 | 0 | 16 | 42 | 43 |
| 3000 | 4 | 3 | −2 | 1 | 19 | 45 | 45 |

* in this case a cross-linked haemoglobin was used.

Example 2

Determination of Alkaline Phosphatase According to the IFCC Method

Determination according to the recommendations of the International Federation of Clinical Chemistry according to J. Clin. Chem. Clin. Biochem. vol. 21, 731–748 (1983).

The determination was carried out on a Boehringer Mannheim/Hitachi 911 analyzer.

The following reagents were used:

reagent 1: 360 mmol/l 2-amino-2-methyl-1-propanol buffer pH 10.4 (30° C.);
2.04 mmol/l magnesium acetate; 1.02 mmol/l zinc sulphate;
2.04 mmol/l N-(2-hydroxyethyl)-ethylenediamine triacetic acid)

reagent 2: 360 mmol/l 2-amino-2-methyl-1-propanol buffer, pH 10.4 (30° C.);
2.04 mmol/l magnesium acetate; 1.02 mmol/l zinc sulphate;
2.04 mmol/l N-(2-hydroxyethyl)-ethylenediamine triacetic acid)
104 mmol/l 4-nitrophenyl phosphate The test procedure was as follows: 250 µl reagent 1 was added to 7 µl sample and after 5 min 60 µl reagent 2 was added. The analyte was determined after a further 50 sec over a period of 4 min during which the change in absorbance was measured during this 4 min. Combinations of the following main measurement wavelengths ($\lambda_1$) and secondary measurement wavelengths ($\lambda_2$) were used for the measurement $\lambda_1/\lambda_2$=415/700 nm (comparison) and 450/480 nm (invention).

TABLE 2-continued

Measured content of alkaline phosphatase at 37° C. in U/l

| Hb content* [mg/dl] | 415/700 nm | 450/480 nm |
| --- | --- | --- |
| 1200 | 139 | 154 |
| 1500 | 133 | 151 |
| 1800 | 126 | 149 |
| 2100 | 123 | 150 |
| 2400 | 116 | 153 |
| 2700 | −4.3 | 154 |
| 3000 | −4.4 | 153 |

*in this case a recombinantly produced haemoglobin was used.

Example 3

Determination of Alkaline Phosphatase According to the DGKC Method

Determination according to the recommendations of the "Deutsche Gesellschaft für Klinische Chemie" according to Z. Klin. Chem. Klin. Biochem. vol. 10, 290 (1972).

The determination was carried out on a Boehringer Mannheim/Hitachi 911 analyzer.

The following reagents were used:

reagent 1: 1.02 mmol/l diethanolamine buffer, pH 9.8; 0.51 mmol/l magnesium chloride,
reagent 2: 1.02 mmol/l diethanolamine buffer, pH 9.8; 0.51 mmol/l magnesium chloride;
61 mmol/l 4-nitrophenyl phosphate The test procedure was as follows: 250 µl reagent 1 was added to 4 µl sample and after 5 min 50 µl reagent 2 was added. The analyte was determined after a further 50 sec over a period of 4 min during which the change in absorbance was measured during this 4 min. Combinations of the following main measurement wavelengths ($\lambda_1$) and secondary measurement wavelengths ($\lambda_2$) were used for the measurement: $\lambda_1/\lambda_2$=415/700 nm (comparison) and 450/546 nm (invention).

The result is shown in table 3. It can be seen that when using the inventive measurement wavelength combination of 450/546 nm the effect of haemoglobin is significantly reduced compared to the previous measurement wavelength combination 415/700 nm and no negative values occur even at very high Hb contents.

TABLE 3

Measured content of alkaline phosphatase at 37° C. in U/l

| Hb content* [mg/dl] | 415/700 nm | 450/546 nm |
|---|---|---|
| 0 | 287 | 298 |
| 650 | 226 | 279 |
| 1300 | 172 | 277 |
| 1950 | 119 | 278 |
| 2600 | 65 | 278 |
| 3250 | 20 | 278 |
| 3900 | −25 | 280 |
| 4550 | −65 | 284 |
| 5200 | −100 | 286 |
| 5850 | −13 | 286 |
| 6500 | −15 | 302 |

*in this case a polymerized haemoglobin was used.

What is claimed is:

1. A method for determining alkaline phosphatase in a sample in which interference by hemoglobin is eliminated, comprising:
   adding 4-nitrophenyl phosphate to said sample;
   simultaneously determining a first optical measurement of said sample at 450±10 nm and a second optical measurement at one or more secondary wavelengths selected from the group consisting of 480±10 nm, 546±10 nm, and 575±10 nm; and
   determinining the difference between the first and second optical measurements.

2. The method of claim 1, wherein the first and second optical measurements comprise absorbance determinations.

3. The method of claim 1, wherein the first and second optical measurements comprise change in absorbance determinations.

4. The method of claim 1, wherein the secondary wavelength is 570 nm.

5. The method of claim 1, wherein said sample comprises a plasma or serum sample.

6. The method of claim 1, wherein said sample comprises a blood substitute.

7. The method of claim 6, wherein the blood substitute comprises derivatized hemoglobin, polymerized hemoglobin, modified hemoglobin, or cross-linked hemoglobin.

8. The method of claim 6, wherein the blood substitute comprises human hemoglobin or bovine hemoglobin.

9. The method of claim 6, wherein the blood substitute comprises a recombinantly-produced hemoglobin.

10. The method of claim 6, wherein the blood substitute comprises diaspirin-crosslinked hemoglobin.

11. The method of claim 1, wherein the secondary wavelength is 480±10 nm.

12. The method of claim 1, wherein said sample has a hemoglobin concentration of up to about 3000 mg/dl.

13. The method of claim 1, wherein said sample has a hemoglobin concentration of up to about 6500 mg/dl.

14. A method for determining a level of alkaline phosphatase in a sample containing 4-nitrophenyl phosphate in which interference by hemoglobin is eliminated, the method comprising:
   simultaneously determining a first optical measurement at 450±10 nm and a second optical measurement at a secondary wavelength selected from the group consisting of 480±10 nm, 546±10 nm, and 575±10 nm; and
   determining the difference between the first and second optical measurements.

15. The method of claim 14, wherein the first and second optical measurements comprise absorbance determinations.

16. The method of claim 14, wherein the first and second optical measurements comprise change in absorbance determinations.

17. The method of claim 14, wherein the secondary wavelength is 570 nm.

18. The method of claim 14, wherein the secondary wavelength is 480±10 nm.

19. A method for determining a level of alkaline phosphatase in a sample in which interference by hemoglobin is eliminated, comprising:
   adding 4-nitrophenyl phosphate to said sample;
   simultaneously measuring a first change in absorbance of said sample at 450±10 nm and
   a second change in absorbance of said sample at 480±10 nm, 546±10 nm, or 575±10 nm; and
   determining the difference between the first and second changes in absorbance.

20. The method of claim 19, wherein the measuring a second change in absorbance of said sample is conducted at 570 nm.

21. The method of claim 19, wherein the measuring a second change in absorbance of said sample is conducted at 480±10 nm.

* * * * *